(12) United States Patent
Perez De La Iglesia

(10) Patent No.: US 9,033,910 B2
(45) Date of Patent: May 19, 2015

(54) TRANSDERMAL DRUG DELIVERY BRACELET

(76) Inventor: Marta Perez De La Iglesia, Madrid (ES)

( * ) Notice: Subject to any disclaimer, the term of this patent is extended or adjusted under 35 U.S.C. 154(b) by 191 days.

(21) Appl. No.: 13/699,484

(22) PCT Filed: Apr. 13, 2011

(86) PCT No.: PCT/ES2011/070249
§ 371 (c)(1),
(2), (4) Date: Jan. 18, 2013

(87) PCT Pub. No.: WO2011/161286
PCT Pub. Date: Dec. 29, 2011

(65) Prior Publication Data
US 2014/0144179 A1  May 29, 2014

(51) Int. Cl.
*A61N 1/30* (2006.01)
*A44C 5/00* (2006.01)
*A61M 35/00* (2006.01)

(52) U.S. Cl.
CPC .............. *A44C 5/0023* (2013.01); *A44C 5/003* (2013.01); *A61M 35/00* (2013.01); *A61M 2202/049* (2013.01)

(58) Field of Classification Search
None
See application file for complete search history.

(56) References Cited

U.S. PATENT DOCUMENTS

| 4,622,035 | A | 11/1986 | Palmer et al. |
| 5,135,480 | A * | 8/1992 | Bannon et al. .................. 604/20 |
| 5,622,293 | A | 4/1997 | LeFevre |
| 2003/0110549 | A1 | 6/2003 | Yeager |

FOREIGN PATENT DOCUMENTS

| WO | WO 2004/052425 | 6/2004 |
| WO | WO 2006/009776 | 1/2006 |
| WO | WO 2006/118479 | 11/2006 |
| WO | WO 2010/034053 | 4/2010 |

OTHER PUBLICATIONS

International Search Report prepared by the Oficina Espanola de Patentes Y Marcas, for International Application No. PCT/ES2011/070249, dated Aug. 10, 2011 (Translation).

* cited by examiner

*Primary Examiner* — Anand Desai
*Assistant Examiner* — Melissa Mercier
(74) *Attorney, Agent, or Firm* — Sheridan Ross P.C.

(57) ABSTRACT

The invention relates to a bracelet that is suitable for the transdermal delivery of various substances. The invention relates to, for example, a refillable, hollow bracelet that contains the substance and that is also provided with a filter that enables the product to be absorbed when in contact with the skin of the user. A mechanism enables the supply of said substance to be totally or partially interrupted. Additionally, the bracelet has a refilling device for refilling the bracelet when the substance runs out.

3 Claims, 2 Drawing Sheets

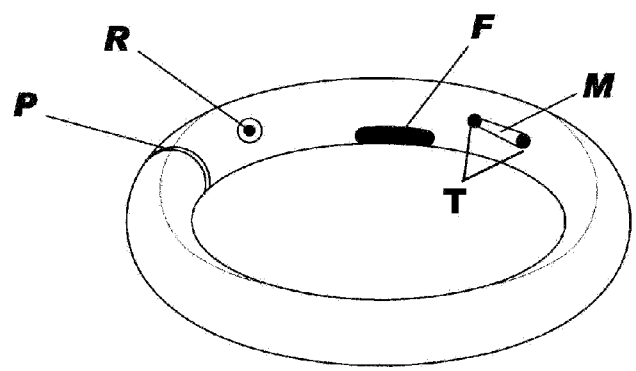
- Fig. 1 -
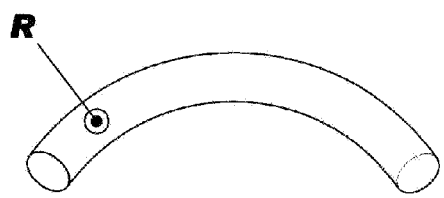
- Fig. 2 -
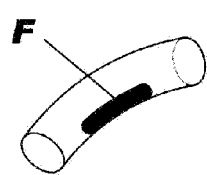
- Fig. 3 -
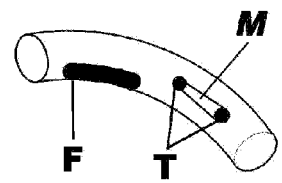
- Fig. 4 -

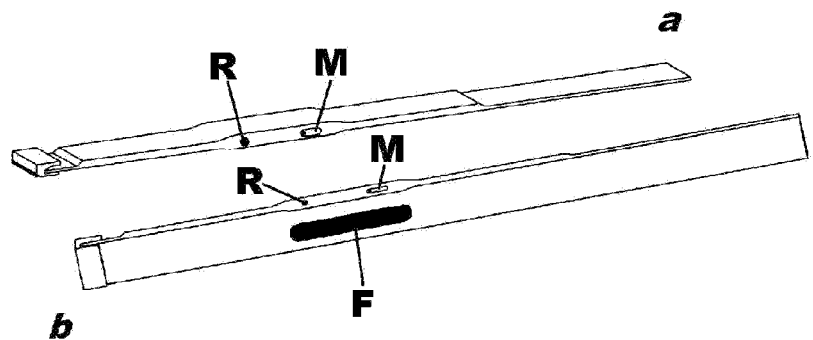
- Fig. 5 -
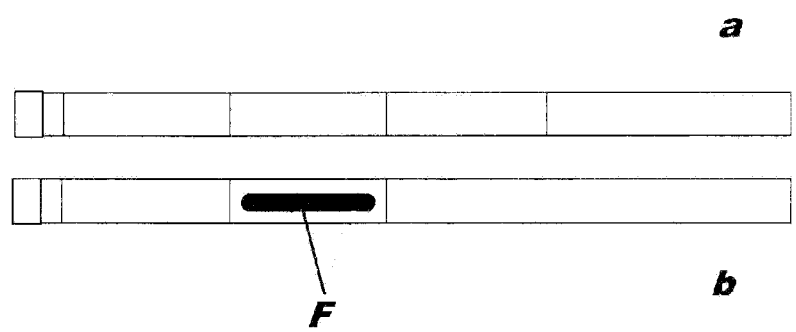
- Fig. 6 -
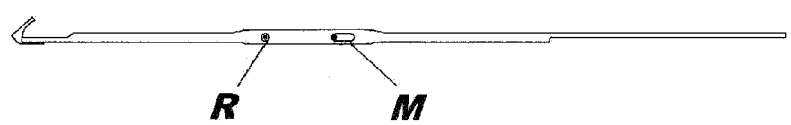
- Fig. 7 -

TRANSDERMAL DRUG DELIVERY BRACELET

CROSS REFERENCE TO RELATED APPLICATION

This application is a national stage application under 35 U.S.C. 371 of PCT Application No. PCT/ES2011/070249 having an international filing date of Apr. 13, 2011, which designated the United States, which PCT application claimed the benefit of Spanish Patent Application No. U201000663, filed on Jun. 22, 2010, both of which are incorporated by reference in their entirety.

INDUSTRIAL SCOPE

The present invention relates to a bracelet provided with a supplier device for substances such as nicotine, fragrances, hormones or any other product susceptible of being transdermally delivered. This invention has been conceived and manufactured so that it can be refilled, and the absorption of the substance can be controlled.

STATE OF THE PRIOR ART

Several substances supplier devices are known, including various types of patches that adhere directly to the skin. This system is rather unattractive and it has the disadvantage of having to be replaced daily. Ad hoc chewing gums are also well known, as well as creams and liquids. These also have disadvantages: chewing gum is not always allowed or correct, such as in exhibitions or working meetings.

No other supplier device provided with a filter in contact with the skin and with a mechanism enabling the right supply of the substance is known.

Regarding inventions of similar bracelets, the American patent U.S. Pat. No. 3,680,751, invented by Walter R. Ten Brook, filed on 31 Jul. 1970, entitled "bracelet for carrying medicinal pills", consists of a hollow bracelet designed to fit the wrist, which is actually a pill container.

Probably the most similar existing patents are the Spanish P200702097, "Perfume dispenser bracelet, convertible to perfume dispenser armband", and its further improvement, P200702443. These bracelets are, however, rigid and split in two halves. The perfume is dispensed through small holes, and they are not intended for transdermal use. Therefore, these bracelets have no filter and there is no control over the amount of substance absorbed.

DESCRIPTION OF THE INVENTION

This bracelet presents a beautiful simple new transdermal delivery of various substances. The object of the invention is based on a hollow refillable bracelet which contains the substance inside, and a filter which is in contact with the skin, so that the product can be gradually absorbed by the user. In order to help controlling the supply, it also contains a mechanism for wholly or partially cut the supply when not needed. Besides, the bracelet also has a refilling device, so the bracelet can be refilled when running out of the substance.

Naturally, there are many different models, such as round bracelets, rigid or flexible, etc, of which we are describing two types.

BRIEF DESCRIPTION OF THE DRAWINGS

On the first page, we have depicted a rigid round bracelet.
FIG. 1 shows an overview of the hollow bracelet.
FIG. 2 shows the refilling device.
FIG. 3 shows the filter in contact with the skin, and
FIG. 4 the mechanism for opening and closing the filter.
On the second page, we have depicted a flexible hollow bracelet.
FIG. 5 comprises two perspective views of the bracelet.
On FIG. 6 a top and a bottom view of the bracelet can be seen. Letters a and b indicate the upper part -a- and lower part -b-.
FIG. 7 is a side view.

DETAILED ACCOUNT OF ITS MANUFACTURING

Since the figures described above, it can be seen that the Spanish invention U201000663 is a rigid hollow bracelet -P in FIG. 1-, containing the substance to be delivered inside. This substance is applied to the skin through the supplying filter -F in FIGS. 1 and 3- allowing the delivery of the substance in appropriate amounts when the bracelet is worn on the wrist and the filter is in contact with the skin. The bracelet also has a refilling device -R in FIGS. 1 and 2-, that allows to refill the bracelet with the substance to be absorbed when exhausted. This refilling device is fitted to an external element for refilling. As shown, the refilling device -R may include a refill opening or hole.

The bracelet contains a mechanism to regulate the product supply-M in FIGS. 1 and 4- , by closing totally or partially. This mechanism can be open or closed at any time, thus controlling the supply of the product according to the needs of the users.

Partially closed and wide open positions are represented on FIGS. 1 and 4 in which a tab T is used to control opening and closing. Thus, the substance to absorb is efficiently supplied and it can be easily controlled, whether by wearing or not the bracelet, or by opening and closing the mechanism.

As it could be easy to imagine, these types of bracelets can be produced in many shapes, so we have considered convenient to describe another manufacturing of the invention: a flexible bracelet. In both cases, obviously, the bracelet should be hollow.

In case of a flexible bracelet, depicted on FIGS. 5, 6 and 7, the filter F (FIG. 7) is located on the underside of the bracelet -b-, in contact with the user's skin. It can be made of different materials and have different thickness, depending on its use.

The opening and closing mechanism M allows to supply the adequate amounts of the substance to be absorbed. The mission of the refilling device R is to refill the bracelet with the adequate substance.

Regarding its use, we have already mentioned its application: 1) in order to control the withdrawal symptoms, in the case of nicotine, 2) for supplying pharmaceutical products, such as hormones, and 3) for supplying fragrances, perfumes or similar substances that smell. It is clear, however, that hollow bracelets with devices that allow the supplying and refilling of a substance to be absorbed can have multiple uses, all of which must be included within the attributable protection of the described invention, as well as any other jewelry, such as brooches, necklaces, rings, etc. based on the transdermal drug delivery through the procedure described above.

The invention claimed is:
1. A transdermal delivery bracelet comprising:
a bracelet having a body that is hollow, and said body filled with a substance to be supplied to a user by absorption; and
a supplying filter integral with bracelet body to control transmission of the substance to the user.

2. The transdermal delivery bracelet, according to claim 1, further including:
   a mechanism including a tab that controls an amount of the supplied substance.

3. The transdermal delivery bracelet, according to claim 1, further including:
   refill opening incorporated on the body of the bracelet for refilling of the substance within the bracelet.

* * * * *

UNITED STATES PATENT AND TRADEMARK OFFICE
CERTIFICATE OF CORRECTION

| | | |
|---|---|---|
| PATENT NO. | : 9,033,910 B2 | Page 1 of 1 |
| APPLICATION NO. | : 13/699484 | |
| DATED | : May 19, 2015 | |
| INVENTOR(S) | : Marta Perez De La Iglesia | |

It is certified that error appears in the above-identified patent and that said Letters Patent is hereby corrected as shown below:

In the Claims

At Column 3, line 7, prior to "refill opening" insert -- a --.

Signed and Sealed this
Twentieth Day of October, 2015

Michelle K. Lee
*Director of the United States Patent and Trademark Office*